United States Patent
Schleifenbaum et al.

(10) Patent No.: US 7,348,035 B2
(45) Date of Patent: Mar. 25, 2008

(54) CYCLODEXTRIN PARTICLE

(75) Inventors: Birgit Schleifenbaum, Crans pres Celigny (CH); Sven Siegel, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 525 days.

(21) Appl. No.: 10/476,828

(22) PCT Filed: Sep. 2, 2003

(86) PCT No.: PCT/EP03/09713

§ 371 (c)(1),
(2), (4) Date: Nov. 3, 2003

(87) PCT Pub. No.: WO2004/022642

PCT Pub. Date: Mar. 18, 2004

(65) Prior Publication Data

US 2004/0234479 A1    Nov. 25, 2004

(30) Foreign Application Priority Data

Sep. 4, 2002 (DE) ............... 102 40 698

(51) Int. Cl.
*A23L 1/22* (2006.01)
(52) U.S. Cl. ................. 426/534; 426/650
(58) Field of Classification Search ............. 426/285, 426/534, 535, 536, 537, 538, 650, 651
See application file for complete search history.

(56) References Cited

U.S. PATENT DOCUMENTS

| 4,946,654 A | 8/1990 | Uhlemann et al. |
| 5,234,610 A | 8/1993 | Gardlik et al. |

FOREIGN PATENT DOCUMENTS

| CN | 1073711 A | 6/1993 |
| CN | 1188143 A | 7/1998 |
| DE | 31 05 666 A1 | 1/1982 |
| EP | 0 163 836 A1 | 3/1985 |
| EP | 0 392 608 A2 | 4/1990 |

OTHER PUBLICATIONS

Hisamitsu Phamaceut Co. Inc. Chemical Abstracts Service, "Formation of Inclusion Compounds of Drugs with Cyclodextrin in Presence of Water-Soluble Polymers to Improve Solibility and Stability", XP002262258, Abstract & Patent Abstracts of Japan, vol. 1995, No. 9, Oct. 31, 1995.
Kodama KK, Chemical Abstracts Service, "Sustained-release Pharmaceuticals Containing Ethyl Cellulose, Glycerides and Cyclodextrin" XP002262259, Abstract, Oct. 11, 1983.

*Primary Examiner*—Leslie Wong
(74) *Attorney, Agent, or Firm*—Akerman Senterfitt; Stephen Pendorf (57) ABSTRACT

The present invention concerns flavor and/or fragrance containing cyclodextrin particles containing cellulose ether with a particle size in the range of from 50 to 1000 μm, products containing these particles, a process for producing as well use in consumables, pharmaceutical products and everyday articles.

19 Claims, 1 Drawing Sheet

X = chewing duration in minutes
Y = peppermint flavor intensity
A = chewing gum with liquid peppermint flavor
B = chewing gum with liquid peppermint flavor + peppermint flavor-particles

FIGURE 1

CYCLODEXTRIN PARTICLE

CROSS REFERENCE TO RELATED APPLICATION

This application is a national stage of PCT/EP03/09713 filed Sep. 2, 2003 and based upon DE 102 40 698.7 filed Sep. 4, 2002 under the International Convention.

BACKGROUND OF THE INVENTION

1. Field of the Invention

The present invention concerns flavor and/or fragrance containing cyclodextrin particles containing cellulose ether with a particle size in the range of 50 to 1000 µm, products containing these particles, a process for their manufacture as well as their use in consumables, pharmaceutical products and everyday articles.

2. Description of the Related Art

Cyclodextrins are oligomers of anhydroglucose units, which are linked via alpha-1,4 linkages into a ring shaped molecule. Depending upon the number of the units one refers to these as alpha (6 unit), beta (7 unit) and gamma (8 unit) cyclodextrin. These are conventionally produced from starch by enzymatic processes. The torroidal structure of the cyclodextrin makes possible the formation of an enclosing complex on a molecular level. Depending upon the geometry and polarity of the flavor material it is possible to form more-or-less stable complexes with the guest molecule resting stably in the polar cyclodextrin cavity.

Flavor substances are generally unstable compounds, which exhibit high rates of loss during storage or during processing for example in the foodstuff industry, due to evaporation or oxidation. The cyclodextrin complexes can protect these flavor substances against these losses.

In the case of flavor materials and fragrance materials, or as the case may be, flavors and fragrance mixtures, these are generally volatile, generally liquid substances, or as the case may be, complex mixtures of these substances. It is conventional to encapsulate these substances or substance mixtures by spray drying; however, generally only relatively fine and irregularly structured particles are obtained.

For the production of complexes of flavor and/or fragrance substances enclosed with cyclodextrin, various methods are known.

These methods include the mixing of cyclodextrin solutions, suspensions or pastes (generally in water) and the flavor and/or aroma substances. Depending upon the polarity of the flavor and/or fragrance substance, there results thereby usually a two-phase mixture. For accelerating this process one thus employs elevated shear forces, for example involving stirring or kneading. Subsequently there is generally a drying step, for example spray drying, freeze drying or fluidized bed drying.

According to the known state of the art, the product of drying by spray drying aqueous aroma/cyclodextrin complexes without additives is very fine particles.

EP-A 392 608 describes a method for producing powdered cyclodextrin complexes, of which the particle size is less than 12, preferably less than 5 µm. Therein processes such as, for example, spray drying and freeze-drying are employed.

This small particle size is disadvantageous for practical use. Fine particle cyclodextrin complexes can only be dispersed in water with difficulty; the solubilization speed is thereby reduced. Besides this, in the case of employment of small (typically <10 µm) cyclodextrin particles in dry mixtures, which primarily include main components with a particle size of between 50 and 500 µm, there is a danger of de-mixing.

In addition, in the case of small particle sizes, it is disadvantageous that often the pourability or flowability is reduced and dust easily develops.

For this reason it is of advantage when the cyclodextrin complex particles have particle sizes of at least 50 µm.

During spray drying, a portion of the flavor and/or fragrance substances remain on the surface of the particles. This so-called surface oil leads to a reduction in the oxidation stability and further reduces the pourability. It is preferred to have the proportion of surface oil as low as possible.

DE-A 31 05 666 describes a process wherein particles with a particle size of 500 to 1000 µm are produced by adding a binder to cyclodextrin complex mixtures in a kneader with subsequent drying and grinding.

Disadvantageous with such kneading process is the high proportion of surface oil in the finished granules. Besides this, with regard to the manufacturing costs, the use of multiple process steps (kneading, drying, grinding, sifting) is disadvantageous.

In EP-A 1 064 856, particles containing carbohydrates and/or polyhydroxy compounds with sizes in the range of 100 to 400 µm are described. The therein disclosed multi-stage process for producing these particles includes, in addition to spray drying, further steps. One of the steps involves the return of smaller particles formed in the process, so that these grow into the desired particle size range by agglomeration. These particles are disadvantageous in their low handling stability and their surface oil content.

BRIEF SUMMARY OF THE INVENTION

The task of the present invention is comprised therein, to provide flavor and/or fragrance containing cyclodextrin particles with a size of at least 50 µm, which avoid the above-described disadvantages according to the state of the art and provide a simple as possible process for production of such particles. In addition, a narrow particle size distribution would be advantageous.

DETAILED DESCRIPTION OF THE INVENTION

The subject of the present invention is thus flavor and/or fragrance containing cyclodextrin particles with a particle size in the range of 50 to 1000 µm containing a cellulose ether obtainable by a one step fluidized bed process from a spray mixture, wherein the gas inlet temperature lies at 80 to 180° C. and the gas exit temperature at 40 to 95° C.

A further aspect of the present invention is a process for producing cyclodextrin particles, thereby characterized, that in a first stage fluidized bed device an aqueous spray mixture is introduced that contains at least one cyclodextrin, at least one flavor and/or fragrance substance and at least one cellulose ether.

The invention further concerns products containing the inventive cyclodextrin particles as well as the use of the inventive cyclodextrin particles in consumables, pharmaceutical products and everyday articles.

For producing the particles from the spray mixture various known processes for granulation can be employed. The useful process according to the invention is single-stage, that is, the spray mixture is supplied to a device and, upon leaving the device, the manufacturing is already completed and the finished cyclodextrin particles are available. In contrast to the multi-stage processes, no intermediate products are produced in the single-stage process.

The particles can be produced by continuous fluidized bed spray granulation, for example according to EP-A 163 836, or by discontinuous fluidized bed spray granulation, for example according to EP-A 70 719. Further, a process such as disclosed in WO-A 97/16078 for production of flavor granules in a conventional discontinuous operated fluidized bed rotor granulator may be employed.

The invention is preferably carried out continuously. A continuous process is better suited for industrial production and exhibits shorter dwell times. For the same material throughput, bed content in the continuous process of the fluidized bed spray granulation is lower than in the case of a discontinuous process. Instead of allowing all particles to grow at the same time, in the continuous fluidized bed spray granulation only a small amount of particle nuclei are sprayed, and, following achievement of the desired particle size, they are immediately discharged, for example via an air separator. The encapsulated flavor and/or aroma cyclodextrin particles produced in accordance with the invention exhibit a small particle size distribution; besides this the particles (granules) can be removed selectively at the desired size.

In the framework of the present invention, it is preferred that the fluidized bed has a small bed height. Preferably this is 3 to 5 cm, in particularly preferred is 5 to 20 cm.

By continuous fluidized bed spray granulation, there results from the spray mixture free flowing, low dust, granular particles. Therein, in the ideal case, there occurs simultaneously in a granulation apparatus the basic processes of nucleus production, drying, formation and selective discharge of the particles that have reached the desired particle size.

The basic principle of continuous fluidized bed spray granulation (Chemical Engineering Technology, 62 year (1990), page 822 through 834) has been realized in countless variations. One can distinguish in particular the variants with external nuclei formation, in which nuclei from external sieves, grinders or other solids storage devices are dosed or metered into the bed, as well as variants with internal nuclei formation.

In the framework of the present invention, processes with internal nuclei supply are preferred. One of these is described for example in EP-A 163 836. This granulation device further utilizes a self-regulating mechanism for particle size regulation and thus involves minimal dwell time.

The spray mixture can be sprayed from below, from the side, or even from above into the fluidized bed. For separation of entrained solids from the exhaust, countless variants are possible, which can be distinguished by the separation process (for example cyclone or filter) or by the location of the separation step (within or outside of the granulation apparatus).

Finally, for the discharge of particles, air separators are preferably employed, for example as described in EP-A 332 031. With the air separators, it is accomplished that only the large particles are able to leave the fluidized bed. The remaining particles remain in the fluidized bed until they have reached the desired particle size.

For production of the inventive particles, first an aqueous spray mixture is produced. This spray mixture contains, besides water, at least one cyclodextrin, at least one flavor and/or fragrance substance as well at least one cellulose ether.

From this spray mixture, the inventive particles with the particle size of greater than or equal to 50 µm are produced in one process step in a fluidized bed temperature.

Inventive particles have a particle size of 50 µm to 1000 µm. Preferred are particles with a particle size of 70 pm to 500 µm, and particularly preferred are 100 to 300 µm.

The characterization of the particle sizes is with respect to the particle diameter and is taken from the particle distribution curve. This particle distribution curve represents the dependency of the distribution sum $Q_3(x)$ of the particle diameters x. The distribution sum $Q_3(x)$ is the normalized total amount of all particles with a diameter smaller than or equal to x. The particle size $x_{50.3}$ is that particle size at which the distribution sum $Q_3(x)=0.5$. Unless otherwise indicated, all references to particle size in the present text are with respect to the particle size $x_{50.3}$. The index 3 indicates that the type of the measured amount is the volume (Ullmanns Encyclopedia of Technical Chemistry, Volume 3, Process Technology I, $4^{th}$ Edition, Chemical Publications, Weinheim, 1972, pages 24-34).

The particle size determination via volume distribution can occur by laser diffraction (for example with the Master Sizer® MSS Longbench produced by Malvern Instruments Ltd., Malvern, UK).

Suitable cyclodextrins include alpha, beta, gamma as well as substituted cyclodextrins. Preferred are alpha, beta, gamma cyclodextrin or their mixtures, and preferred among these is beta-cyclodextrin. In a preferred embodiment, the cyclodextrin of the spray mixture is comprised solely of beta-cyclodextrin.

The proportion of cyclodextrin in the spray mixture is preferably 5 to 50 wt. %, preferably 10 to 40 wt. %, and particularly preferably 15 to 30 wt. %.

The proportion of water in the spray mixture is preferably 40 to 95 wt. %, more preferably at 50 to 90 wt. %, most preferably 60 to 80 wt. %.

The proportion of flavor and/or fragrance in the spray mixture is preferably 0.0005 to 15 wt. %, more preferably 0.5 to 10 wt. %, most preferably 0.25 to 5 wt. %.

The spray mixture contains, as granulation aid, a binder, namely cellulose ether. The cellulose ether is preferably selected from the group including methylcellulose, ethylcellulose, propylcellulose, hydroxyethylcellulose, hydroxypropylcellulose, hydroxy-propylmethylcellulose, carboxymethylcellulose, carboxymethylhydroxyethylcellulose and ethylhydroxyethylcellulose; particularly preferred is carboxymethylcellulose (CMC).

The cellulose ether content of the spray mixture is preferably 0.1 through 6 wt. %, particularly preferably from 0.2 to 2 wt. %. The dried particles preferably contain between 0.5 and 10 wt. %, particularly preferably between 2 and 4.5 wt. % cellulose ethers.

Preferred are cellulose ethers with a viscosity of 15 to 200,000 mPas, more preferred are those with a viscosity of 1,000 to 50,000 mPas, most preferred are those with a viscosity of 5,000 to 15,000 mPas. The viscosity characteristics are determined with a 2 wt. % solution in water at 20° C.

As measuring system there is used a conical plate system with a diameter of 40 mm and a cone angle of 4°. The temperature is 20° C., the shear rate is 1 $s^{-1}$. The viscosity can be determined using, for example a rheometer CVO 120 (produced by Bohlin Instruments GmbH, Pforzheim, Germany).

Following the inventive process, the proportion of flavor and/or fragrance in the finished cyclodextrin particles is 0.01 to 30 wt. %, preferably 1 to 15 wt. % and particularly preferably 5 to 10 wt. %.

Methods for determining the loading of the surface oil are known from the literature. In the present case the determination of the content of flavor and/or fragrance substances in the finished cyclodextrin particles, for determining the loading of the surface oil, was carried out analogously to J. Agric. Food Chem. 1998, 46, 1494-1499. The methods described there were deviated from essentially with respect to the solvents used for extraction. In place of n-hexane, ethylacetate was used for determining the loading and for determining the surface oil proportion a 2:1 mixture (volumetric proportion) of n-pentane and diethylether were employed in place of n-hexane. Loading and surface oil proportion were indicated in wt. %.

Examples of flavor and/or fragrance substances, which can be a component of the inventive cyclodextrin particles, can be found for example in S. Arctander, Perfume and Flavor Chemicals, Vol. I and II, Montclair, N.J., 1969, self publication or K. Bauer, D. Garbe and H. Surburg, Common Fragrance and Flavor Materials, 4$^{th}$ Ed., Wiley-VHC, Weinheim 2001.

Individual substances include the following: Extracts of natural raw materials such as essential oils, concretes, absolutes, resins, resinoids, balms, tinctures such as e.g., ambergris tincture; amyris oil; angelica seed oil; angelica root oil; aniseed oil; valerian oil; basil oil; tree moss absolute; bay (myrcia) oil; motherwort or mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamon seed oil; cascarilla oil; cassia oil; cassia absolute; castoreum absolue; cedar leaf oil; cedar wood oil; cistus oil; citronella oil; lemon oil; copaiba balsam; copaivabalsam oil; coriander oil; costus root oil; cumin oil; cypress oil; davana oil; dill weed oil; dill seed oil; eau de brouts absolue; oak moss absolue; elemi oil; tarragon oil; eucalyptus citriodora oil; eucalyptus oil; fennel oil; fir needle oil; galbanum oil; galbanum resin; geranium oil; grapefruit oil; guaiac wood oil; guaiac balsam; guaiac balsam oil; helichrysum absolue; helichrysum oil; ginger oil; iris root absolute; iris root oil; jasmin absolute; calmus oil; chamomile oil bleu; chamomile oil roman; carrot seed oil; cascarilla oil; pine needle oil; mint oil; carvi oil; labdanum oil; labdanum absolute; labdanum resin; lavandin absolute; lavandin oil; lavender absolute; lavender oil; lemongrass oil; lovage oil; lime oil distilled; lime oil pressed; Bursera penicillata (linaloe) oil; litsea-cubeba oil; bay laurel leaf oil; macis oil; marjoram oil; mandarin oil; massoirinde oil; mimosa absolute; ambrette seed oil; ambrette tincture; muskatelle salbei oil; nutmeg oil; myrrh absolue; myrrh oil; myrtle oil; carnation leaf oil; carnation blossom oil; neroli oil; olibanum absolute; olibanum oil; opopanax oil; orange blossom absolute; orange oil; oregano oil; palmarosa oil; patchouli oil; perilla oil; Peru balsam oil; parsley leaf oil; parsley seed oil; clove seed oil; peppermint oil; pepper oil; pimento oil; pine oil; poley oil; rose absolue; rose wood oil; rose oil; rosmary oil; sage oil; lavandin; sage oil Spanish; sandalwood oil; celery seed oil; lavender spike oil; star anis oil; styrax oil; tagetes oil; pine needle oil; tea-tree oil; turpentine oil; thyme oil; tolu balm; tonka absolute; tuberose absolute; vanilla extract; violet leaf absolute; verbena oil; vetiver oil; juniper berry oil; wine yeast oil; wormwood oil; wintergreen oil; ylang ylang oil; hyssop oil; civet absolute; cinnamon leaf oil; cinnamon bark oil; as well as fractions thereof, or components isolated therefrom;

individual fragrances from the group of carbohydrates, such as e.g. 3-caren; α-pinene; β-pinene; α-terpins; γ-terpines; p-cymene; bisabalol; camphene; caryophyllen; cedrene; farnesene; limonene; longifolene; myrcene; ocimene; valencene; (E,Z)-1,3,5-undecatriene;

aliphatic alcohols such as e.g. hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixtures of 3,4,5,6,6-pentamethyl-3/4-hepten-2-ol und 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; the aliphatic aldehydes and their 1,4-dioxacycloalken-2-one as well as e.g. hexanal; heptanal; octanal; nonanal; decanal; undecanal; dodecanal; tridecanal; 2-methyloctanal; 2-Methylnonanal; (E)-2-Hexenal; (Z)-4-Heptenal; 2,6-Dimethyl-5-heptenal; 10-undecenal; (E)-4-decenal; 2-dodecenal; 2,6,10-trimethyl-5,9-undecadienal; heptanaldiethylacetal; 1,1-dimethoxy-2,2,5-trimethyl-4-hexene; citronellyloxyacetaldehyde;

the aliphatic ketones and their oximes such as e.g. 2-heptanone; 2-octanone; 3-octanone; 2-nonanone; 5-methyl-3-heptanone; 5-methyl-3-heptanonoxime; 2,4,4,7-tetramethyl-6-octen-3-one; the aliphatic sulfur containing compounds such as e.g. 3-methylthiohexanol; 3-methylthiohexylacetate; 3-mercaptohexanol; 3-mercaptohexylacetate; 3-mercaptohexylbutyrate; 3-acetylthiohexylacetate; 1-menthen-8-thiol;

the aliphatic nitriles such as e.g. 2-nonenoic acid nitrile; 2-tridecene acid nitrile; 2,12-tridecadiene acid nitrile; 3,7-dimethyl-2,6-octadiene acid nitrile; 3,7-dimethyl-6-octene acid nitrile;

the aliphatic carboxylic acids and their esters such as e.g. (E)- and (Z)-3-hexenylformate; ethylacetoacetate; isoamylacetate; hexylacetate; 3,5,5-trimethylhexylacetate; 3-methyl-2-butenylacetate; (E)-2-hexenylacetate; (E)- and (Z)-3-hexenylacetate; octylacetate; 3-octlyacetate; 1-octen-3-ylacetate; ethylbutyrate; butylbutyrate; isoamylbutyrate; hexylbutyrate; (E)- and (Z)-3-hexenylisobutyrate; hexylcrotonat; ethylisovalerianate; ethyl-2-methylpentanoate; ethylhexanoate; allylhexanoate; ethylheptanoate; allylheptanoate; ethyloctanoate; ethyl-(E,Z)-2,4-decadienoate; methyl-2-octinate; methyl-2-noninate; allyl-2-isoamyloxyacetate; methyl-3,7-dimethyl-2,6-octadienoate;

the acyclic terpene alcohols such as e.g., citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as their formates, acetates, propionates, isobutyrates, butyrates, isovalerianates, pentanoates, hexanoates, crotonates, tiglinates, 3-methyl-2-butenoates;

the acyclic terpene aldehydes und-ketones such as e.g. geranial; neral; citronellal; 7-hydroxy-3,7-dimethyloctanal; 7-methoxy-3,7-dimethyloctanal; 2,6,10-trimethyl-9-undecenal; geranylacetone; as well as the dimethylund diethylacetales of geranial, neral, 7-hydroxy-3,7-dimethyloctanal;

the cyclic terpene alcohols such as e.g. menthol; isopulegol; alpha-terpineol; terpinenol-4; menthan-8-ol; menthan-1-ol; menthan-7-ol; borneol; isoborneol; linalooloxide; nopol; cedrol; ambrinol; vetiverol; guaiol; as well as their formiates, aceates, propionates, isobutyrate, butyrate, isovalerianates, pentanoates, hexanoates, crotonates, tiglinate, 3-methyl-2-butenoates;

the cyclic terpenaldehydes and ketones such as e.g. menthone; isomenthone; 8-mercaptomenthan-3-one; carvone; camphor; fenchon; alpha-ionon; beta-ionon; alpha-n-methylionon; beta-n-methylionon; alpha-isomethylionon; beta-isomethylionon; alpha-irone; alpha-damascone; beta-damascone; beta-damascenone; delta-damascone; gamma-damascon; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedar wood oil (methylcedrylketone);

the cyclic alcohols such as e.g. 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedrylmethylether; cyclododecylmethylether; (ethoxymethoxy)cyclododecane; alpha-cedrenepoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-dien; roseoxide; 2-(2,4-dimethyl-3-cyclohexen-1-yl)-5-methyl-5-(1-methylpropyl)-1,3-dioxan;

the cyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetra-methylcyclohexanone; 4-tert-pentylcyclohexanone; 5-cyclohexadecen-1-one; 6,7-dihydro-1,1,2,3,3-pentamethyl-4(5H)indanone; 5-cyclohexadecen-1-one; 8-cyclohexadecen-1-one; 9-cycloheptadecen-1-one; cyclopentadecanone;

the cycloaliphatic aldehydes such as e.g. 2,4-dimethyl-3-cyclohexencarbaldehyde; 2-methyl-4-(2,2,6-trimethylcyclohexen-1-yl)-2-butenal; 4-(4-hydroxy-4-methylpentyl)-3-cyclohexencarbaldehyde; 4-(4-methyl-3-penten-1-yl)-3-cyclohexencarbaldehyde;

the cycloaliphatic ketones such as e.g. 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienylketone; tert-butyl-(2,4-dimethyl-3-cyclohexen-1-yl)ketone;

the esters of cyclic alcohols such as e.g. 2-tert-butylcyclohexylacetate; 4-tert butylcyclohexylacetate; 2-tert-pentylcyclohexylacetate; 4-tert-pentylcyclohexylacetate; decahydro-2-naphthylacetate; 3-pentyltetrahydro-2H-pyran-4-ylacetate; decahydro-2,5,5,8a-tetramethyl-2-naphthylacetate; 4,7-methano-3a,4,5,6,7,7a-hexahydro-5, or 6-indenylacetate; 4,7-methano-3a,4,5,6,7,7a-hexahydro-5, or 6-indenylpropionate; 4,7-methano-3a,4,5,6,7,7a-hexahydro-5, or 6-indenylisobutyrate; 4,7-methanooctahydro-5, or 6-indenylacetate;

the esters of cycloaliphatic carboxylic acids such as e.g. allyl-3-cyclohexylpropionate; allylcyclohexyloxyacetate; methyldihydrojasmonate; methyljasmonate; methyl-2-hexyl-3-oxocyclopentancarboxylate; ethyl-2-ethyl-6,6-dimethyl-2-cyclohexencarboxylate; ethyl-2,3,6,6-tetramethyl-2-cyclohexencarboxylate; ethyl-2-methyl-1,3-dioxolan-2-acetate;

the aromatic carbohydrates such as e.g. styrene und diphenylmethane;

the araliphatic alcohols such as e.g. benzylalcohol; 1-phenylethylalcohol; 2-phenylethylalcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethylalcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzylalcohol; 1-(4-isopropylphenyl)ethanol;

the esters of araliphatic alcohols and aliphatic carboxylic acids such as e.g. benzylacetate; benzylpropionate; benzylisobutyrate; benzylisovalerianate; 2-phenylethylacetate; 2-phenylethylpropionate; 2-phenylethylisobutyrate; 2-phenylethylisovalerianate; 1-phenylethylacetate; alpha-trichlormethylbenzylacetate; alpha,alpha-dimethylphenylethylacetate; alpha,alpha-dimethylphenylethylbutyrate; cinnamylacetate; 2-phenoxyethylisobutyrate; 4-methoxybenzylacetate; the araliphatic ethers such as e.g. 2-phenylethylmethylether; 2-phenylethylisoamylether; 2-phenylethyl-1-ethoxyethylether; phenylacetaldehyde dimethylacetal; phenylacetaldehyde-diethylacetal; hydratropaaldehyde dimethylacetal; phenylacetaldehyde glycerinacetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

the aromatic and araliphatic aldehyde such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylendioxybenzaldehyde; 3,4-dimethoxybenzaldehyde; 2-methyl-3-(4-methoxyphenyl)propanal; 2-methyl-3-(4-methylendioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanylmethylketone; 6-tert-butyl-1,1-dimethyl-4-indanylmethylketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-aceto-naphthone;

the aromatic and araliphatic carboxylic acids and their esters such as e.g. benzoic acid; phenylacetic acid; methylbenzoate; ethylbenzoate; hexylbenzoate; benzyl-benzoate; methylphenylacetate; ethylphenylacetate; geranylphenylacetate; phenylethyl-phenylacetate; methylcinnamate; ethylcinnamate; benzylcinnamate; phenylethylcinnamate; cinnamylcinnamate; allylphenoxyacetate; methylsalicylate; isoamylsalicylate; hexylsalicylate; cyclohexylsalicylate; cis-3-hexenylsalicylate; benzylsalicylate; phenylethylsalicylate; methyl-2,4-dihydroxy-3,6-dimethylbenzoate; ethyl-3-phenylglycidate; ethyl-3-methyl-3-phenylglycidate;

the nitrogen containing aromatic compounds such as e.g. 2,4,6-trinitro-1,3-dimethyl-5-tert-butylbenzol; 3,5-dinitro-2,6-dimethyl-4-tert-butylacetophenone; cinnamic acid nitrile; 5-phenyl-3-methyl-2-pentene acid nitrile; 5-phenyl-3-methylpentane acid nitrile; methylanthranilate; methy-N-methylanthranilate; Schiff's bases of methylanthranilate with 7-hydroxy-3,7-dimethyloctanal, 2-methyl-3-(4-tert-butylphenyl)propanal or 2,4-dimethyl-3-cyclohexencarbaldehyde; 6-isopropylchinolin; 6-isobutylchinolin; 6-sec-butylchinolin; indol; skatole; 2-methoxy-3-isopropylpyrazine; 2-isobutyl-3-methoxypyrazine;

the phenols, phenylethers und phenylesters such as e.g. estragole; anethole; eugenole; eugenylmethylether; isoeugenole; isoeugenylmethylether; thymol; carvacrol; diphenylether; beta-naphthylmethylether; beta-naphthylethylether; beta-naphthylisobutylether; 1,4-dimethoxybenzol; eugenylacetate; 2-methoxy-4-methylphenol; 2-ethoxy-5-(1-propenyl)phenol; p-cresylphenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis-und trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylen-1,12-dodecandioate; ethylen-1,13-tridecandioate; coumarin; 2,3-dihydrocoumarin; octahydrocumarin.

Examples of aromatic substances that would be suitable as components of the cyclodextrine particles are, besides all the above mentioned compounds, primarily the following classes of compounds: aliphatic esters (saturated and unsaturated) e.g. ethylbutyrate, allylcapronate; aromatic esters e.g. benzylacetate, methylsalicylate; organic aliphatic acids (saturated and unsaturated) e.g. butyric acid, acetic acid, caprionic acid; organic aromatic acids; aliphatic alkohols (saturated and unsaturated) e.e. ethanol, propylene glycol, octenol, 3-ocetenol, cis-3-hexenol; cyclic alcohols e.g. menthol; aromatic alcohols e.g. benzyl alcohol; aliphatic aldehydes (saturated and unsaturated) e.g. acetaldehyde, nonadienal; aromatic aldehyde e.g. benzaldehyde; ketone e.g. menthon; cyclic ethers e.g. 4-hydroxy-5-methylfuranone; aromatic ether e.g. p-methoxybenzaldehyde, guaiacol; phenolic ethers e.g. methoxyvinylphenol; acetale e.g. acetaldehyde diethylacetal; lactones e.g. gamma-decalactone; terpenes e.g. limonene, linalool, terpines, terpineol, citral (geranial und neral); sulfur containing compounds e.g. dimethylsulfide, methylthiol, ethylthiol, allylisothiocyanate, methylfuranthiol, difurfuryldisulfide or pyrazine e.g. methylpyrazine, acetylpyrazine.

Due to the very small proportion of surface oil on the inventive cyclodextrin particles, these are particularly suitable for encapsulation of very fragrance-intensive, very volatile, easily oxidized, difficult to control and/or pour substances. There can be mentioned in this context for example acetaldehyde, allylisothiocyanate, limonene, cis-3-hexenol, citral, methylethylpyrazine or methylthiol.

Besides this, the inventive cyclodextrin articles can contain nutritional compounds or mixtures of compounds (nutraceuticals). There can be mentioned for example panthenol, pantothenic acid, essential fatty acids, Vitamin A und derivates, carotine, Vitamin C (ascorbic acid), Vitamin E (tocopherol) and derivates, vitamins of the B- and D-series such as Vitamin $B_6$ (nicotinamide), Vitamin $B_{12}$, Vitamin $D_1$, Vitamin $D_3$, Vitamin F, folic acid, biotin, amino acids, compounds of the elements magnesium, silicon, phosphorus, calcium, manganese, iron or copper, coenzym Q10, unsaturated fatty acids, ω-3-fatty acids, polyunsaturated fatty acids, γ-linolic acid, oleic acid, eicosapentaoic acid, docosahexanoic acid and their derivates, bisabolol, chloramphenicol, caffein, capsaicin, prostaglandin, thymol, camphor, extracts or other products of plant and animal origin, e.g. evening primrose oil, borage oil or currant seed oil, fish oil, cod liver oil, ceramide and ceramide like compounds. Plant extracts such as e.g. arnika, aloe, barbers' itch, ivy, stinging nettles, ginseng, henna, chamomile, ringlet flower, rosemary, legend (*Folia Salviae*), box blade or thyme. Oils such as apricot seed oil, avocado oil, babassu oil, cotton seed oil, borage oil, thistle oil, peanut oil, gamma-oryzan oil, haws seed oil, hemp oil, hazelnut oil, currant seed oil, jojoba oil, cherry seed oil, salmon oil, flax oil, corn oil, macadamia nut oil, almond oil, evening primrose oil, mink oil, olive oil, pecan nut oil, plum seed oil, pistachio nut oil, rape seed oil, rice germ oil, castor oil plant oil, safflower oil, sesame seed oil, soy oil, sunflower oil, tea tree oil, grapes kernel oil or wheat germ oil.

It is of course possible that the inventive cyclodextrin particles can include further substances such as for example emulsifiers, colorants, anti-oxidants, stabilizers, UV-absorbers, vitamins and other ingredients conventional in the consumable, body care, pharmaceutical or flavor and fragrance industry.

The production of the spray mixture can occur for example as described in EP-A 1 084 625 or as described below.

First, a complex of cyclodextrin and the flavor substance is formed. For this, cyclodextrin and flavor must be brought at least partially into solution. As solvent, one could employ water at a temperature of 10° C. to 90° C., preferably from 40° C. to 70° C., particularly preferably 50 to 60° C. For flavor substances with particularly low boiling points or high temperature sensitivities, temperatures of 15 to 30° C. are preferred.

Depending upon the polarity of the flavor and/or fragrance substance, the result is usually a two-phase mixture. Shear forces are preferably used to accelerate the process. The introduction of the shear forces can occur, for example by stirring or, as the case may be, dispersing, wherein rotor-stator dispersing apparatus or high pressure homogenizers, among others, are suitable.

The movement or biasing of the true equilibrium in the direction of the flavor and/or fragrance cyclodextrin complex takes time. In accordance with the invention, the batch is stirred with introduction of shear forces preferably 0.2 to 24 hours with cooling to 4 to 25° C., preferably 8 to 16 hours with cooling to 4 to 7° C.

In the case of sensitive or delicate flavor and/or fragrance substances the rest time is preferably shortened to 15 to 30 minutes at 4 to 7° C.

The addition of cellulose ethers into the spray mixture can occur at any point in time. This could be prior to complex formation, during complex formation, following complex formation but prior to cool storage, during cool storage or after cool storage. It is also possible to mix the cellulose ether with the cyclodextrin powder and subsequently to introduce the mixture into the water. The addition of the total amount of the cellulose ether can also be subdivided into multiple fractions, which is proportioned, and added at varying time points.

In the production of the spray mixture, the addition of the feed stock can occur in any sequence. For example, cyclodextrin and cellulose ether can be mixed, subsequently added to water and intensively stirred or, as the case may be, dispersed. Subsequently flavor and/or fragrance substances can be added and the mixture intensively stirred or, as the case may be, dispersed and cool stored. An alternative sequence comprises first the intensive mixing of water, cellulose ether and flavor and/or fragrance substance as well as the subsequent addition and the dispersion of cyclodextrin. In a further exemplary variation, cyclodextrin can be added to water and intensively stirred. The flavor is added to this and dispersed. Following the subsequent cool storage, the cellulose ether is added and distributed by stirring or, as the case may be, dispersing.

Granulation occurs preferably at a granulation temperature as described in EP-A 163 836. The temperature of the spray mixture is selected in such a manner that there is no decomposing or destabilizing of the flavor or, as the case may be, fragrance cyclodextrin complex. The temperature is generally between 5 and 70° C., preferably between 10 and 40° C. and particularly preferably between 20 and 30° C.

As fluidizing gas, one could employ, for example air, nitrogen, argon or carbon dioxide, and preferred are air and nitrogen. The gas inlet and gas outlet temperatures of the fluidizing gas are to be adapted to the respective spray mixtures. The gas inlet temperature is between 80 and 180° C., preferably between 100 and 140° C., and particularly preferably between 120 and 130° C. The gas outlet temperatures lies between 40 and 95° C., preferably between 45 and 70° C., particularly preferably between 50 and 60° C.

The inventive cyclodextrin particles can be employed in a variety of products. In nutritional and snack goods these could be employed for example in sweets such as for example hard candies, chewing gum, breath mints, comprimates, hard caramels, confectioneries and chocolate, baked good such as cakes, waffles or wafers and small cakes, snacks, instant meals as well as other instant products (soups, sauces, powdered and granulated drinks, tea bags, spice mixtures). The cyclodextrin particles are particularly suitable for heated, high heated, warmed, sterilized or pasteurized consumables such as, for example, catered foods, fried foods, chips, flavored panades, precooked foods, microwave foods as well as fruits and vegetable preserves.

Pharmaceutical products can include for example dissolvable tablets, throat or cough lozenges, pharmaceutical powders or granulates.

Everyday articles could be, for example, body care products, house care products, tobacco wares, (for example cigarettes), cosmetic products, laundry, dishwashing or detergent compositions, air fresheners, textiles or odor absorbing substances, for example cat litter.

Body care products can include for example oral care products such as toothpaste, tooth gel, dental creams, dental care gum and mouth wash.

The following examples further explain the invention:

Unless indicated otherwise, all proportions are with respect to weight.

The term retention (indicated in wt. %) will in the present case be understood to mean the weight-dependent relationship of the amount of flavor and/or fragrance substance in the finished particle in comparison to the amount of flavor and/or fragrance substance employed in the spray mixture.

EXAMPLES

Example 1

Limonene—Cyclodextrin Particle

Ingredients:
13,143 g drinking water
4,000 g beta-cyclodextrin (Kleptose® beta-cyclodextrin, produced by Roquette)
431 g d-limonene
133 g carboxymethylcellulose (CMC)(Walocel CRT 10000 GA available from the company Wolff Walsrode, Germany)
viscosity of a 2% solution at 20° C., 1 s$^{-1}$: 1,000 mPas The water was warmed to 25° C., the cyclodextrin was added and the formulation was mixed for 3 minutes using an Ultra Turrax T50 DPX. The d-limonene was added, and the batch was dispersed for an additional 15 minutes.

After the mixture was stored for 6 hours at 6° C., the carboxymethylcellulose was added and homogenized using the Ultra Turrax T50 DPX. Thereafter, the batch was stirred for an additional 15 hours at 20° C. and subsequently introduced into the fluidized bed granulation apparatus.

In a granulation apparatus of the type described in EP-A 163 836 (with the following features: diameter inflow base: 225 mm, spray nozzle: 2-material nozzle; fluidized output: zigzag air separator; filter: internal hose filter), the above described spray mixture was granulated. The temperature of the mixture was at 35° C. For fluidizing the bed content, air in an amount of 60 kg/h was blown in. The inlet temperature of the fluidized gas was at 120° C. The temperature of the output gas was at 55° C. As separating gas, air in amount of 1.5 kg/h was supplied at a temperature of 34° C. The granulation yield was approximately 420 g/h. A free flowing granulate with an average particle size of 131.7 µm and a flow density of 470 g/l was obtained. The granulate exhibited a flat surface and spherical, substantially ball-shaped geometry.

On the basis of the constant pressure loss of the filter and the likewise constant remaining bed content, this can be referred to as a stationary condition with respect to the granulation process.
load: 7.7%
retention: 79.2%
surface oil: 0.03%
particle size distribution (using laser diffraction; device: Malvern Master Sizer® MSS Longbench):
$Q_3(x)=0.1$: $x=75$ µm
$Q_3(x)=0.5$: $x=132$ µm
$Q_3(x)=0.9$: $x=196$ µm
powder density: 470 g/l Example 2

Limonene Particle 2

6,385 g drinking water
2,000 g beta-cyclodextrin
215.5 g d-limonene
78 g carboxymethylcellulose (CMC), Tylose® C 6000 G1 produced by the company Clariant
viscosity of a 2% solution at 20° C., 1 s$^{-1}$ mPas: 6,000 mPas The water was warmed to 50° C., the cyclodextrin was added, and the formulation was stirred for 3 minutes using an Ultra Turrax T50 DPX. The d-limonene was added and the batch was dispersed for an additional 15 minutes.

After the mixture was stored for 30 minutes at 20° C., the carboxymethylcellulose was added and homogenized with the help of the Ultra Turrax mixer.

Thereafter, the batch was allowed to rest for an additional 15 hours at 6° C. and was subsequently supplied to the fluidized bed granulation apparatus of Example 1. The inlet temperature of the fluidizing gas was 125° C. The temperature of the output gas was 49° C. Granulation produced approximately 570 g/h. A free flowing granulate with an average particle size of 165.8 μm and a powder density of 460 g/l was obtained. The cyclodextrin particles exhibited a flat outer surface and a spherical, substantially ball shaped geometry.

loading: 8.4%
retention: 86.4%
surface oil: 0.04%
particle size relationship (laser diffraction):
  $Q_3(x)=0.1$: x=89 μm
  $Q_3(x)=0.5$: x=166 μm
  $Q_3(x)=0.9$: x=272 μm
powder density: 460 g/l Example 3

Peppermint Aroma Particles 6,385 g drinking water
2,000 g beta-cyclodextrin
215.5 g peppermint aroma
62 g carboxymethylcellulose (CMC) (Walocel CRT 1000 GA of the company Wolff Walsrode, Germany)
viscosity of the 2% solution at 20° C., 1 $s^{-1}$ mPas: 10,000 mPas The water was warmed to 50° C., the cyclodextrin was added and the batch was mixed for 3 minutes with an ultra turrax T50 DPX. After addition of the peppermint aroma, the batch was mixed thoroughly for an additional 15 minutes with the ultra turrax T50 DPX. CMC was added and dissolved with the ultra turrax.

The storage and further production occurred analogous to Example 2, the granulation output was 600 g/h. A free flowing granulate was obtained.

loading: 8.8%
retention: 87%
particle size distribution (as determined by laser diffraction; device: Malvern Master Sizer® MSS Longbench):
  $Q_3(x)=0.1$: x=103 μm
  $Q_3(x)=0.5$: x=182 μm
  $Q_3(x)=0.9$: x=296 μm
surface oil: 0.03%
powder density: 400 g/l Example 4

Beef Flavor Particles 6,385 g drinking water
2,000 g beta-cyclodextrin
200 g beef meat flavor
95 g methylcellulose (MC), Methocel® A4M FG, Dow Chemical Company
viscosity of a 2% solution at 20° C., 1 $s^{-1}$ mPas: 4,000 mPas After addition of the cyclodextrin in water (10° C.) the formulation was stirred for 3 minutes with an Ultra Turrax T50 DPX. The beef meat flavor was added and the batch was dispersed for an additional 40 minutes. After the mixture has allowed to rest for 30 minutes at 20° C. the methylcellulose was added and homogenized with the Ultra Turrax mixer.

Storage and further production occurred analogously to Example 1.

Examples 5-14

Composition of spray mixtures, the indication is with respect to the employed amount in gram.

| | 5 | 6 | 7 | 8 | 9 | 10 | 11 | 12 | 13 | 14 |
|---|---|---|---|---|---|---|---|---|---|---|
| water | 6200 | 6000 | 6000 | 6385 | 6385 | 6500 | 6500 | 6385 | 6800 | 6900 |
| alpha-cyclodextrin | 660 | 2000 | 0 | 0 | 0 | 0 | 0 | 0 | 0 | 0 |
| beta-cyclodextrin | 660 | 0 | 0 | 2000 | 2000 | 2000 | 2000 | 2000 | 2000 | 2000 |
| gamma-cyclodextrin | 660 | 0 | 2000 | 0 | 0 | 0 | 0 | 0 | 0 | 0 |
| carboxymethylcellulose (Walocel ® CRT 10000 GA) | 55 | 55 | 55 | 0 | 0 | 0 | 0 | 0 | 0 | 0 |
| hydroxypropylmethylcellulose methocel ® K4MFG | 0 | 0 | 0 | 90 | 0 | 0 | 0 | 0 | 0 | 0 |
| ethylcellulose | 0 | 0 | 0 | 0 | 60 | 0 | 0 | 0 | 0 | 0 |
| propylcellulose | 0 | 0 | 0 | 0 | 0 | 70 | 0 | 0 | 0 | 0 |
| hydroxyethylcellulose Tylose MH 4000 P2 | 0 | 0 | 0 | 0 | 0 | 0 | 90 | 0 | 0 | 0 |
| hydroxypropylcellulose | 0 | 0 | 0 | 0 | 0 | 0 | 0 | 60 | 0 | 0 |
| ethylhydroxyethylcellulose | 0 | 0 | 0 | 0 | 0 | 0 | 0 | 0 | 60 | 0 |
| carboxymethylhydroxyethylcellulose | 0 | 0 | 0 | 0 | 0 | 0 | 0 | 0 | 0 | 90 |
| lemon oil | 200 | 150 | 230 | 10 | 1 | 250 | 100 | 50 | 200 | 75 |

Example 15

Comparison

In Table 1, the advantages with respect to oxidation stability, flowability and redispersibility of the particles produced in accordance with the invention as compared to particles that are produced in accordance with the state of the art become clear. The better oxidation stability is determined by the lower proportion of surface oil.

TABLE 1

| Cyclodextrin-Particles containing d-limonene | According to the invention | per EP-A 392 608 | per DE-A 31 05 666 | |
|---|---|---|---|---|
| Embodiment | Example 2 | Kneading, spray drying | Kneading, drying grinding, sifting | |
| Process | Batchwise preparing of the spray mix, continuous, simultaneous drying and granulation | Batchwise preparing of the spray mix, continuous simultaneous drying and no granulation | Continuous extrusion and granulation | Batchwise preparation of the mix, batch drying, batch grinding, batch sifting |
| Particle size | 50 μm-300 μm | 0.05 μm-5 μm | 500-1000 μm | 500-1000 μm |
| Pourability (angle of pouring) | 32° | 63° | 52° | 47° |
| Redispersibility at 20° C. | 4 | 0 | 3 | 3 |
| Surface oil | 0.04% | 0.40% | 2.4% | 0.19% |
| Retention | 86% | 74% | 92% | 86% |
| Oxidation sensitivity (after 180 days) | 0 | 3 | 5 | 3 |

Flowability was determined in accordance with DIN ISO 4324. A pour angle <300 means a very good flowability, a pour angle between 30° and 40° means a free flowability and a pour angle >45° means a poor flowability (see also Uhlemann, Moehrl: Fluidized Bed Spray Granulation, Springer-Publishers Berlin, 2000, page 169).

Oxidation sensitivity was evaluated following storage times of one day or, as the case may be, 180 days (storage temperature 20° C.). Respectively 100 g samples were filled into a 250 ml plastic bottle which was tightly closed with a lid. Following the respective storage times the bottles were opened and evaluated as to smell. The evaluation was based on a scale of 0 (no oxidation smell) to 5 (strong oxidation smell). After one day all particles of Table 1 were still in basically sound condition.

Redispersibility was checked in the following way: in a beaker glass 20 ml water (20° C.) and 200 mg of the respective particles were added and stirred for 1 minute at 200 min$^{-1}$ with a magnetic stirrer. Evaluation was based on a scale of 0 (very poor redispersibility) to 5 (complete redispersibility). Very poor redispersibility was indicated when, following the stirring, not all of the particles were wetted or hydrated with water, had formed large agglomerates and/or if following a stand time of 1 minute, many particles sank to the floor.

Example 16

Chewing Gum with Peppermint Flavor

Figure 1:
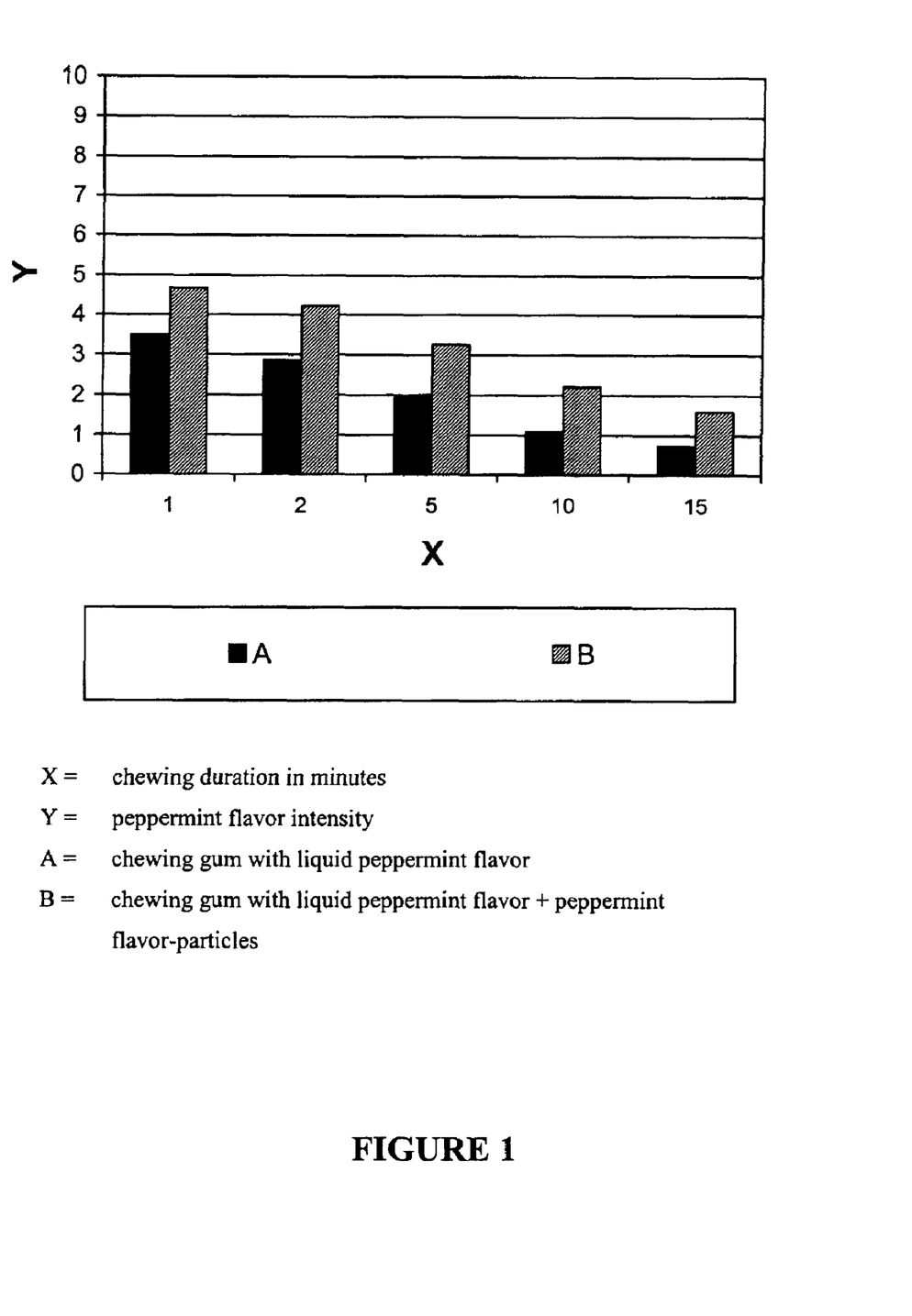

In a chewing gum (B) 2 wt. % of peppermint flavor-cyclodextrin product of Example 3 (corresponding to 0.18 wt. % flavor) and 1.12 wt. % peppermint flavor in fluid form were worked in. For comparison, a chewing gum (A) was produced, which contained 1.30 wt. % peppermint flavor in liquid form. Sensory time-intensity studies using a skilled test group (12 persons) showed overall a significantly higher flavor intensity with chewing gum (B) with peppermint flavor-particles. These results are summarized in FIG. 1. As shown in FIG. 1, after 15 minutes the peppermint flavor-cyclodextrin product (A) containing sample had twice as high a flavor intensity as the control product (B).

The peppermint flavor intensity was evalated on a scale of from 0 (no peppermint flavor) to 10 (very strong peppermint flavor).

Example 17

Wafers

The limonene-cyclodextrin product of Example 2 was added in an amount of 1.2 wt. % (corresponding to 0.1 wt. % flavor) to a wafer batter comprised of flour, water, sugar, lecithin, salt and peanut oil. Wafers were baked at a temperature of 200° C. for 1 minute. For comparison, liquid limonene was added in the same concentration to the batter and mixed into the same ingredients. The sensory evaluation of fresh product (1 day old) demonstrated a higher flavor intensity in the wafers with the limonene-cyclodextrin product. As shown in Table 2, sensory evaluation could be confirmed.

TABLE 2

|  | Wafers with 0.1 wt. % limonene as cyclodextrin complex | Wafers with 0.1% limonene (liquid) |
| --- | --- | --- |
| Limonene content in the baked wafer | 2533 ppm | 755 ppm |
| Retention following baking | 95% | 38% |
| limonene-note (following storage) | 3 | 0 |
| Off-flavor | 0 | 4 |
| Sensorial description | fresh, citrus | flat, oxidized, rancid |

The sensory evaluation of the flavor intensity of the limonene note and the off-flavor occurred following 4-month storage at 20° C., on a scale of from 0 (not detectable) to 5 (very strong).

The term retention (indicated in %) is in the present case understood to mean the weight based relationship of the amount of limonene in the waffle in comparison to the employed amount of limonene.

Example 18

Instant Soup

To a powder mixture comprising salt, starch, seasoning powder, fat powder and dried vegetable were added, for reinforcing the fresh green note, cis-3-hexenol-cyclondextrin particles, which were produced analogously to Example 1.

As a result of the employed particle size of 100 to 200 μm, the following properties were found during the mixing process: free of dust, low danger of coming out of mixture, good flowability.

During the storage, cis-3-hexenol in the cyclodextrin complex was well protected against oxidization, in particular on the basis of the low proportion of surface oil in the particles produced in accordance with the present invention.

Following pouring of the instant soup mixture into water at 80° C., the complex dissolves within a few seconds.

The invention claimed is:

1. A flavor or fragrance containing a cyclodextrin particle comprising said cyclodextrin particle and a flavor or fragrance,
   wherein said cyclodextrin particle has 0.04% or less surface oil,
   wherein said cyclodextrin particle has a particle size in a range of 50 to 1000 μm,
   wherein said cyclodextrin particle comprises cellulose ether,
   wherein said cyclodextrin particle is obtained by a single stage fluidized bed process from a spray mixture, and
   wherein a gas introduction temperature is from 80 to 180° C. and a gas outlet temperature is from 40 to 95° C.

2. The flavor or fragrance containing said cyclodextrin particle according to claim 1, wherein said cellulose ether is selected from the group consisting of methylcellulose, ethylcellulose, ethylhydroxyethyl-cellulose, propyl-cellulose, hydroxyethylcellulose, hydroxypropylcellulose, hydroxypropylmethylcellulose, carboxymethylhydroxyethyl-cellulose, carboxy-methylcellulose enthalten, and mixtures thereof.

3. The flavor or fragrance containing said cyclodextrin particle according to claim 1, wherein said cellulose ether further comprises carboxymethylcellulose.

4. The flavor or fragrance containing said cyclodextrin particle according to claim 1, wherein said cyclodextrin particle has a particle size in the range from 100 to 300 μm.

5. The flavor or fragrance containing said cyclodextrin particle according to claim 1, wherein said fluidized bed process is a fluidized bed spray granulation process.

6. The flavor or fragrance containing said cyclodextrin particle according to claim 1, wherein said cyclodextrin particle is selected from the group consisting of alpha cyclodextrin, beta cyclodextrin, gamma cyclodextrin, and mixtures thereof.

7. The flavor or fragrance containing said cyclodextrin particle according to claim 6, wherein said cyclodextrin particle is beta cyclodextrin.

8. The flavor or fragrance containing said cyclodextrin particle according to claim 1, wherein an amount of said flavor or said fragrance in said cyclodextrin particle is from 0.01 to 30 wt. %.

9. A product comprising a flavor or fragrance containing said cyclodextrin particle according to claim 1, wherein said product comprises consumables, pharmaceutical products, and everyday articles.

10. A process for producing the cyclodextrin particle according to claim 1, said method comprising:
    spraying an aqueous spray mixture in a single stage fluidized bed device,
    wherein said aqueous spray mixture comprises at least one cyclodextrin, at least one flavor or fragrance, and at least one cellulose ether.

11. The process according to claim 10, wherein a fluidized bed device is a fluidized bed spray granulation apparatus.

12. The process according to claim 10, wherein said aqueous spray is sprayed continuously.

13. The process according to claim 10, wherein the aqueous spray mixture comprises 40 to 95 wt. % water, 5 to 50 wt. % cyclodextrin, 0.0005 to 15 wt. % flavor or fragrance substance, and 0.1 to 6 wt. % cellulose ether.

14. The process according to claim 13, wherein the aqueous spray mixture contains 60 to 80 wt. % water, 15 to 30 wt. % cyclodextrin, 0.25 to 5 wt. % flavor or fragrance substance, and 0.2 to 2 wt. % cellulose ether.

15. The process according to claim 11, wherein a gas in circulated through the a single stage fluidized bed device, where a gas introduction temperature is from 80 to 180° C. and a gas outlet temperature is from 40 to 95° C.

16. A flavor or fragrance containing cyclodextrin particle comprising cyclodextrin, a flavor or fragrance, and a cellulose ether,
    wherein said cyclodextrin particle has a 180 day oxidation sensitivity value of 0,
    wherein said cyclodextrin particle has a particle size in a range of 50 to 1000 μm,
    wherein said cyclodextrin particle is obtained by a single stage fluidized bed process from a spray mixture, and
    wherein a gas introduction temperature is from 80 to 180° C. and a gas outlet temperature is from 40 to 95° C.

17. The flavor or fragrance containing cyclodextrin particle according to claim 16,
wherein said cyclodextrin particle has 0.04% or less surface oil.

18. The flavor or fragrance containing cyclodextrin particle according to claim 16, wherein said cyclodetrin particle has a pourability of 32 degrees of less.

19. The flavor or fragrance containing cyclodextrin particle according to claim 16, wherein said cyclodextrin particle has a redispersability at 20 degrees Celsius of 4 or greater.

* * * * *

UNITED STATES PATENT AND TRADEMARK OFFICE
CERTIFICATE OF CORRECTION

PATENT NO. : 7,348,035 B2  
APPLICATION NO. : 10/476828  
DATED : March 25, 2008  
INVENTOR(S) : Schleifenbaum et al.

Page 1 of 1

It is certified that error appears in the above-identified patent and that said Letters Patent is hereby corrected as shown below:

Column 3, line 66, replace "as well" with -- as well as --

Column 6, line 9, replace "und 3,5,6,6-" with -- and 3,5,6,6- --

Column 6, line 53, replace "und-ketones" with -- and -ketones- --

Column 6, line 56, replace "dimethylund" with -- dimethyl and --

Column 9, line 12, replace "und phenylesters" with -- and phenylesters --

Column 9, line 27, replace "cis-und" with -- cis- and --

Column 9, line 41, replace "e.e. ethanol" with -- e.g. ethanol --

Column 9, line 51, replace "geranial und neral" with -- geranial and neral --

Column 9, line 65, replace "Vitamin A und" with -- Vitamin A and --

Column 15, line 41, replace "a pour angle <300 means" with -- a pour angle <30° means --

Column 18, line 52, replace "the a single" with -- the single --

Column 19, line 6, replace "cyclodetrin" with -- cyclodextrin --

Signed and Sealed this

Twentieth Day of January, 2009

JON W. DUDAS  
*Director of the United States Patent and Trademark Office*